United States Patent [19]  [11] 4,145,367
Boozalis et al.  [45] Mar. 20, 1979

[54] PROCESS FOR PURIFYING 1,2-DICHLOROETHANE

[75] Inventors: Theodore S. Boozalis; John B. Ivy, both of Lake Jackson, Tex.

[73] Assignee: The Dow Chemical Company, Midland, Mich.

[21] Appl. No.: 547,521

[22] Filed: Feb. 6, 1975

[51] Int. Cl.$^2$ .............................................. C07C 21/02
[52] U.S. Cl. .............................. 260/652 P; 260/656 R
[58] Field of Search ............. 260/652 P, 654 S, 656 R

[56] References Cited

U.S. PATENT DOCUMENTS

| | | | |
|---|---|---|---|
| 2,748,176 | 5/1956 | Morris | 260/652 P |
| 3,125,607 | 3/1964 | Keating et al. | 260/656 R |
| 3,125,608 | 3/1964 | McDonald | 260/656 R |

*Primary Examiner*—Delbert E. Gantz
*Assistant Examiner*—Joseph A. Boska
*Attorney, Agent, or Firm*—G. R. Baker

[57] ABSTRACT

A process for removing chlorinated hydrocarbon impurities from 1,2-dichloroethane streams by partially or completely hydrogenating some or all of the impurities therein by passing hydrogen into said stream in the presence of a palladium hydrogenation catalyst under conditions which do not promote the decomposition of the ethylene dichloride in said stream.

4 Claims, No Drawings

PROCESS FOR PURIFYING 1,2-DICHLOROETHANE

BACKGROUND OF THE INVENTION

In the manufacture of vinyl chloride by the thermal dehydrochlorination of 1,2-dichloroethane, the 1,2-dichloroethane is passed through a cracking furnace. A portion of the 1,2-dichloroethane emerges from the furnace unreacted and is recycled to increase vinyl chloride yield. In addition to vinyl chloride, small quantities of other partially chlorinated compounds such as chloroprene and trichloroethylene are also produced. These impurities must be removed from the unconverted 1,2-dichloroethane before it can be returned to the furnace because they cause reduced dehydrochlorination rates in the cracking furnaces, and they polymerize, inhibiting the flow of reactants and products in the process.

Attempts to remove these impurities from recycle 1,2-dichloroethane streams by distillation have not been entirely satisfactory because some of the impurities polymerize in the stills when they are concentrated. Further, stills which are capable of carrying out these distillations are major capital investments. It would, therefore, be advantageous to provide a process for removing the impurities and eliminate these attendant problems in both the stills and the furnaces.

BRIEF DESCRIPTION OF THE INVENTION

In accordance with the present invention the impurities in a recycle stream from a thermal ethylene dichloride dehydrochlorination process (the stream obtained following removal of the vinyl chloride, lights and hydrogen chloride) or any stream of ethylene dichloride containing unsaturated partially chlorinated impurities can be purified by hydrogenation of the stream over a hydrogenation catalyst at temperatures below about 250° C. followed by distillation of the compounds boiling below about 70° C. from the hydrogenated stream.

Good results have been obtained in accordance with the present invention when the amount of hydrogen supplied is at least equal to that theoretically necessary to hydrogenate the chloroprene content of the stream. Preferably, however, the amount of hydrogen should be equal to about that theoretically necessary to hydrogenate not only the chloroprene present but the other unsaturated partially chlorinated hydrocarbon impurities. More than this amount is not harmful but some dehydrochlorination of these partially chlorinated hydrocarbons will occur. The hydrogen in excess of that necessary to hydrogenate the unsaturated impurities does not appear to materially dehydrochlorinate the 1,2-dichloroethane at the temperatures employed in accordance with the invention.

While the invention has described with respect to hydrogenation of the entire stream it is to be understood that the impurities can be concentrated, as by distillation, in a small portion of the stream, i.e., 10 percent or more and this concentrate hydrogenated in the same manner aforedescribed. The product of the hydrogenation being distilled as before, those compounds boiling below 70° C. being removed and the bottoms being joined to the recycle stream from which it was separated. Of course this procedure requires an additional still.

The process can be operated at substantially any pressure, above atmospheric pressure being preferred. Good results have been obtained at from about 50 to over 400 psig. Although greater or lower pressures can be employed, it is not usually economically advantageous to exceed these limits.

The preferred catalyst is palladium. Rhodium is more expensive and promotes the reductive dechlorination reaction, while platinum and ruthenium are too slow for practical applications. Palladium in a support such as silica or carbon gives good results. Silica is the preferred catalyst support due to its ability to withstand high temperature oxidation during catalyst regeneration. The temperature of the hydrogenation must be below about 250° C. in order to prevent the reductive dichlorination of 1,2-dichloroethane.

Since these byproducts represent a yield loss, it would be of further advantage to convert some of these compounds to 1,2-dichloroethane by the same process.

DETAILED DESCRIPTION

EXAMPLE 1

A portion of a production recycle stream was analyzed and the portion distilled to recover a 10 percent by weight cut of the portion containing essentially all the compounds boiling at a lower temperature than 1,2-dichloroethane contained in the portion. The 10 percent cut was hydrogenated for 2.2 hours over 0.1 percent by weight palladium on silica at about 80 psig hydrogen pressure and 60° C. Three molecules of hydrogen were fed to the hydrogenation reactor per molecule of chloroprene. The analysis of the so hydrogenated cut is set forth below. Combination of the bottoms of a distillation of this hydrogenated cut with the 90 percent bottoms from the first distillation illustrates the marked reduction in chloroprene, particularly, as well as other partially chlorinated hydrocarbons in the portion.

TABLE FOR EXAMPLE 1

| | Stream A Analysis of a Typical Production Recycle Stream | Stream B Analysis of a 10% By Weight Distillation Cut of Stream A | Stream C Analysis of Stream B After Hydrogenation | Stream D Analysis of 90% Bottoms Cut From Stream A Combined With Bottoms From Distillation of Stream C |
|---|---|---|---|---|
| Ethane | — | — | 0.16 | — |
| Butane | — | — | 0.25 | — |
| Vinyl Chloride | — | — | — | — |
| Ethyl Chloride | — | — | 0.34 | — |
| Vinylidene Chloride | 0.06 | 0.59 | — | — |
| 1-Chlorobutene-1 | — | — | 0.59 | — |
| 1-Chlorobutene-2 | — | — | — | — |
| trans-1,2-Dichloroethylene | 0.08 | 0.83 | 0.56 | — |
| 2-Chlorobutene-1 | — | — | 4.01 | trace |
| Chloroprene | 0.47 | 4.67 | 0.14 | — |

TABLE FOR EXAMPLE 1-continued

|  | Stream A<br>Analysis of a<br>Typical Pro-<br>duction Recycle<br>Stream | Stream B<br>Analysis of a<br>10% By Weight<br>Distillation<br>Cut of Stream<br>A | Stream C<br>Analysis of<br>Stream B After<br>Hydrogenation | Stream D<br>Analysis of 90%<br>Bottoms Cut From<br>Stream A Combined<br>With Bottoms From<br>Distillation of<br>Stream C |
|---|---|---|---|---|
| 2-Chlorobutane | — | — | 0.02 | — |
| 1,1-Dichloroethane | 0.05 | 0.47 | 0.30 | — |
| 2-Chlorobutene-2 | — | — | 0.17 | — |
| 1-Chloro-1,3-Butadiene | 0.07 | 0.73 | — | — |
| 1-Chlorobutane | — | — | 0.06 | — |
| Carbon Tetrachloride | 0.02 | 0.24 | 0.11 | — |
| cis-1,2-Dichloroethylene | 0.10 | 1.03 | 0.72 | — |
| Benzene | — | — | — | — |
| Chloroform | 0.10 | 1.03 | 0.70 | — |
| Trichloroethylene | 0.01 | trace | trace | trace |
| 1,2-Dichloroethane | 98.06 | 90.4 | 91.87 | 99.02 |
| Perchloroethylene | 0.20 | trace | trace | 0.20 |
| 1,1,2-Trichloroethane | 0.78 | — | — | 0.78 |

EXAMPLE 2

A portion of a production recycle stream was analyzed and the entire portion hydrogenated over 1 percent by weight palladium on silica bed. The analysis of the recycle stream before and after hydrogenation and reaction conditions are shown below:

TABLE FOR EXAMPLE 2

| Hydrogen Rate, liter/hour | 2.0 |
|---|---|
| Recycle 1,2-Dichloroethane Rate, liter/hour | 0.191 |
| Catalyst | 1% Pd |
| Reactor Volume, liter | 0.300 |
| Reactor Pressure, psig | 200 |
| Reaction Temperature | 150 |

| Component | Ethylene<br>Dichloride<br>Production<br>Recycle<br>Stream<br>Before<br>Hydro-<br>genation | Ethylene<br>Dichloride<br>Production<br>Recycle<br>Stream<br>After<br>Hydro-<br>genation |
|---|---|---|
| Ethane | — | 0.07 |
| Butane | — | 0.57 |
| Vinyl Chloride | — | — |
| Ethyl Chloride | trace | 0.03 |
| Vinylidene Chloride | 0.02 | — |
| 1-Chlorobutene-1 | — | trace |
| 1-Chlorobutene-2 | — | trace |
| trans-1,2-dichloroethylene | 0.04 | 0.02 |
| 2-Chlorobutene-1 | — | 0.05 |
| Chloroprene | 0.60 | — |
| 2-Chlorobutane | — | 0.06 |
| 1,1-Dichloroethane | 0.02 | 0.02 |
| 2-Chlorobutene-2 | — | 0.01 |
| 1-Chloro-1,3-Butadiene | 0.09 | trace |
| 1-Chlorobutane | — | — |
| Carbon Tetrachloride | trace | trace |
| cis-1,2-Dichloroethylene | 0.11 | 0.02 |
| Benzene | — | — |
| Chloroform | 0.03 | 0.02 |
| Trichloroethylene | trace | trace |
| 1,2-Dichloroethane | 98.69 | 98.75 |
| Perchloroethylene | 0.03 | 0.02 |
| 1,1,2-Trichloroethane | 0.37 | 0.36 |

EXAMPLE 3

A portion of a production recycle 1,2-dichloroethane stream was analyzed and hydrogenated over 0.5 percent by weight palladium on charcoal. The analysis of the recycle before and after hydrogenation is set forth below. These analyses illustrate the elimination of trichloroethylene as well as other partially chlorinated compounds. Operation of the foregoing procedure resulted in a 3 percent by weight increase in 1,2-dichloroethane.

TABLE FOR EXAMPLE 3

| Reaction Temperature, ° C. | 200 |
|---|---|
| Reaction Pressure, psig | 300 |
| Catalyst Volume, liters | 0.1 |
| Ethylene Chloride Feed, liter/hour | 0.2 |
| Hydrogen Rate, mole/hour | 1.0 |

| Component | Ethylene<br>Dichloride<br>Recycle<br>Before<br>Hydro-<br>genation | Ethylene<br>Dichloride<br>Recycle<br>After<br>Hydro-<br>genation |
|---|---|---|
| Ethylene | 0.01 | — |
| Ethane | — | 0.99 |
| Vinyl Chloride | 0.01 | — |
| Ethyl Chloride | — | 0.74 |
| Unknowns | — | — |
| Vinylidene Chloride | 0.01 | — |
| trans-1,2-Dichloroethylene | 0.02 | — |
| Methylene Chloride | 0.01 | 0.12 |
| 1,1-Dichloroethane | 0.04 | — |
| Chloroprene | 0.01 | — |
| Methyl Chloroform | 0.06 | — |
| Carbon Tetrachloride | 0.03 | — |
| cis-1,2-Dichloroethylene | 0.10 | — |
| Benzene | 0.04 | 0.14 |
| Chloroform | 0.15 | — |
| Trichloroethylene | 4.34 | — |
| 1,2-Dichloroethane | 95.17 | 98.01 |

What is claimed is:

1. In a method for removing impurities from a recycle stream from a dehydrochlorination of ethylene dichloride to vinyl chloride, the improvement which comprises hydrogenating over a palladium hydrogenation catalyst at least a part of said recycle stream and distilling from said hydrogenated portion the compounds boiling below about 70° C., said palladium hydrogenation catalyst consisting essentially of from 0.01 to 5 weight percent palladium on an inert support, said hydrogenation being carried out at a temperature of from about 0° C. to below about 250° C., said hydrogen being supplied in an amount at least theoretically sufficient to hydrogenate all the unsaturated impurities.

2. The method of claim 1 wherein said catalyst is 0.1 weight percent palladium on silica.

3. The method of claim 1 wherein the amount of hydrogen supplied is sufficient to theoretically hydrogenate the conjugated ethylenic unsaturation present in said recycle stream.

4. The method of claim 2 wherein said hydrogen is supplied in an amount sufficient to hydrogenate the chloroprene present in said recycle stream.

* * * * *